United States Patent
Song et al.

(10) Patent No.: US 10,695,216 B2
(45) Date of Patent: Jun. 30, 2020

(54) ASSEMBLY AND METHOD FOR DELIVERY OF MICRO-VOLUME DROPLETS FROM A SQUEEZE BOTTLE

(71) Applicant: Nanodropper, LLC, Seattle, WA (US)

(72) Inventors: Allisa Jungha Song, Seattle, WA (US); Elias Lee Baker, Seattle, WA (US)

(73) Assignee: Nanodropper, LLC, Seattle, WA (US)

( * ) Notice: Subject to any disclaimer, the term of this patent is extended or adjusted under 35 U.S.C. 154(b) by 0 days.

(21) Appl. No.: 16/255,152

(22) Filed: Jan. 23, 2019

(65) Prior Publication Data

US 2019/0224044 A1 Jul. 25, 2019

Related U.S. Application Data

(60) Provisional application No. 62/621,052, filed on Jan. 24, 2018.

(51) Int. Cl.
*A61F 9/00* (2006.01)
*B65D 47/18* (2006.01)

(52) U.S. Cl.
CPC ............ *A61F 9/0008* (2013.01); *B65D 47/18* (2013.01)

(58) Field of Classification Search
CPC .............................. A61F 9/0008; B65D 47/18
See application file for complete search history.

(56) References Cited

U.S. PATENT DOCUMENTS

| | | | | |
|---|---|---|---|---|
| 3,612,409 A | * | 10/1971 | Henning | B05B 1/00 239/602 |
| 4,173,226 A | * | 11/1979 | Shell | A61F 9/0017 604/295 |
| 4,471,890 A | * | 9/1984 | Dougherty | B65D 47/18 222/190 |
| 4,605,398 A | * | 8/1986 | Herrick | A61F 9/0026 604/295 |
| 4,739,906 A | * | 4/1988 | LoTurco | A61J 1/1443 222/212 |
| 4,927,062 A | * | 5/1990 | Walsh | B01L 3/0272 222/211 |
| 5,221,027 A | | 6/1993 | Gibilsco | |
| 5,226,568 A | * | 7/1993 | Newton | B65D 47/2081 222/212 |

(Continued)

FOREIGN PATENT DOCUMENTS

| | | |
|---|---|---|
| DK | 2986539 T3 | 8/2018 |
| JP | 2005-211184 A | 8/2005 |

(Continued)

OTHER PUBLICATIONS

International Search Report and Written Opinion issued for PCT/US2019/014717, dated Mar. 20, 2019.

*Primary Examiner* — Frederick C Nicolas
(74) *Attorney, Agent, or Firm* — Westman, Champlin & Koehler, P.A.; Amanda M. Prose

(57) ABSTRACT

A method and assembly for attaching to a container and configured to reduce the volume of a droplet of fluid ejected from the container wherein the assembly is securable to the container without alteration of the container and wherein the volume of the droplet is reduced on a microliter scale. The assembly comprises a base for securing a neck of the container; a tip for securing over a dispensing outlet of the container; and optionally a cap for securing over the tip and connecting to the base.

19 Claims, 4 Drawing Sheets

(56) References Cited

U.S. PATENT DOCUMENTS

| | | | |
|---|---|---|---|
| 5,261,572 A * | 11/1993 | Strater | B65D 47/18 222/215 |
| 5,358,151 A | 10/1994 | Strasenburgh | |
| 5,373,972 A | 12/1994 | Bystrom et al. | |
| 5,611,788 A | 3/1997 | Marchment | |
| 6,197,008 B1 | 3/2001 | Hagele | |
| 6,257,429 B1 * | 7/2001 | Kong | A61J 9/001 215/11.3 |
| 6,632,202 B1 | 10/2003 | Hagele | |
| 6,991,121 B1 * | 1/2006 | Kipperman | A61J 9/005 215/11.1 |
| 7,537,141 B1 | 5/2009 | Robinson | |
| 7,563,256 B2 | 7/2009 | Hearne | |
| 7,758,553 B2 | 7/2010 | Poisson et al. | |
| 7,846,140 B2 | 12/2010 | Hagele | |
| 8,287,505 B2 | 10/2012 | Pine | |
| 8,496,635 B2 * | 7/2013 | Katayama | A61F 9/0008 604/298 |
| 8,517,222 B2 * | 8/2013 | Painchaud | B65D 47/18 222/212 |
| 8,820,549 B1 * | 9/2014 | Estrada | A61J 9/001 215/11.3 |
| 2003/0024947 A1 | 2/2003 | Joshi et al. | |
| 2004/0074925 A1 | 4/2004 | Faurie | |
| 2006/0116649 A1 | 6/2006 | Hagele | |
| 2006/0191959 A1 | 8/2006 | Davies et al. | |
| 2007/0051362 A1 | 3/2007 | Sullivan et al. | |
| 2009/0212133 A1 | 8/2009 | Collins, Jr. | |
| 2009/0259204 A1 | 10/2009 | Galdeti et al. | |
| 2009/0272769 A1 * | 11/2009 | Contreras | B65D 1/08 222/420 |
| 2015/0038925 A1 | 2/2015 | Parunak et al. | |

FOREIGN PATENT DOCUMENTS

| | | |
|---|---|---|
| WO | 2014055676 A1 | 4/2014 |
| WO | 2014170736 A1 | 10/2014 |

* cited by examiner

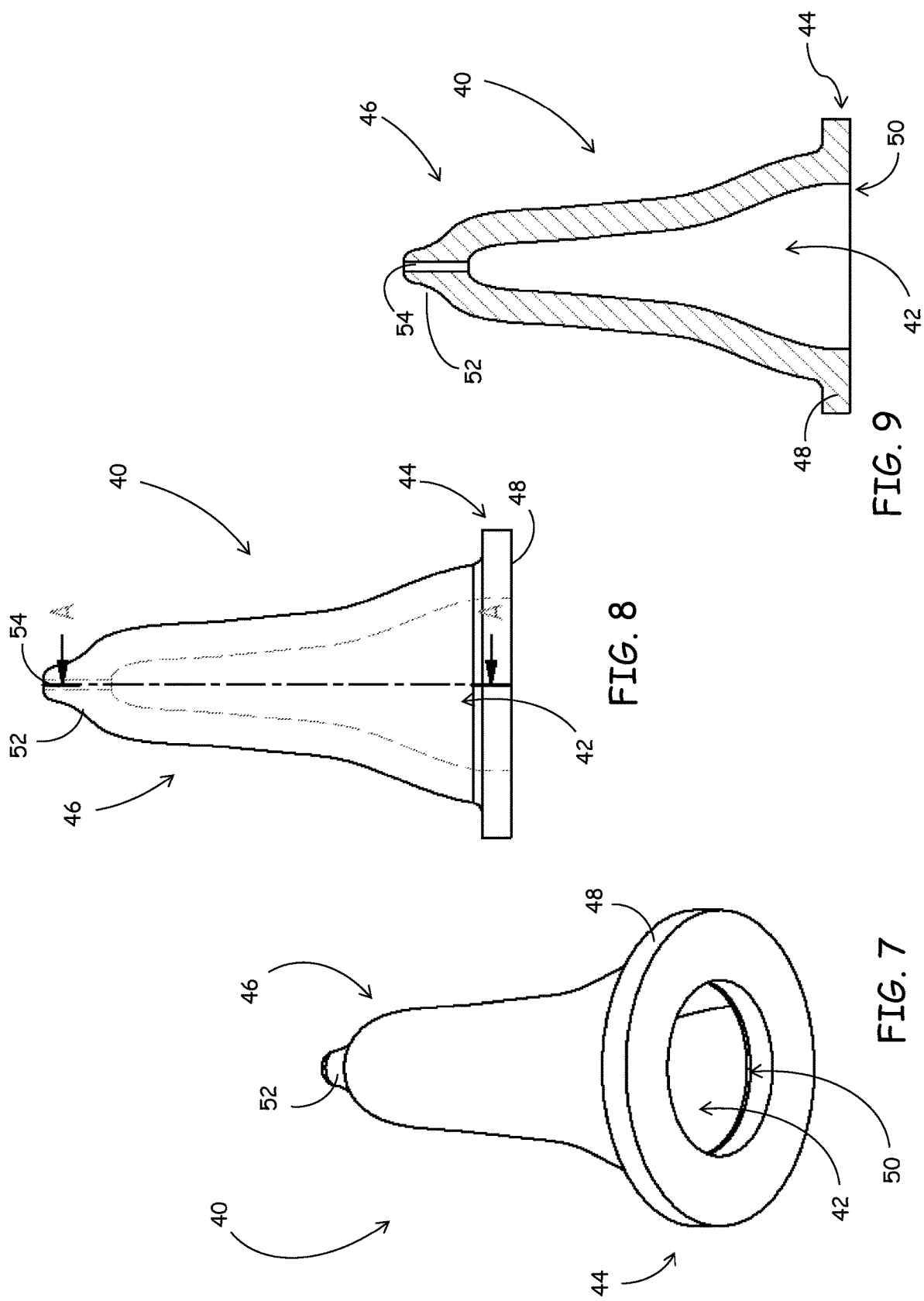

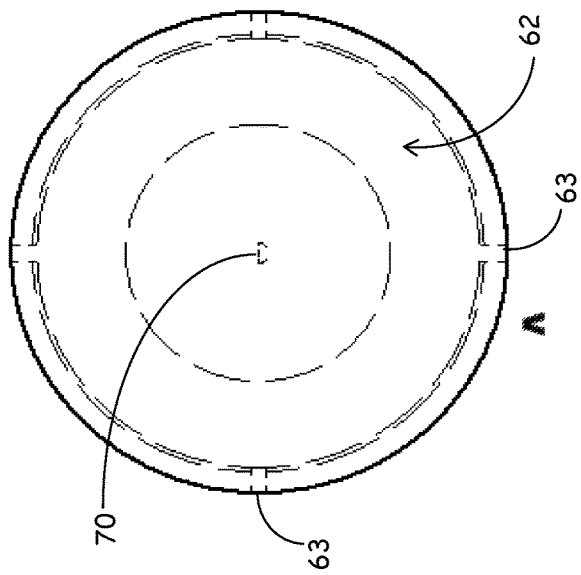
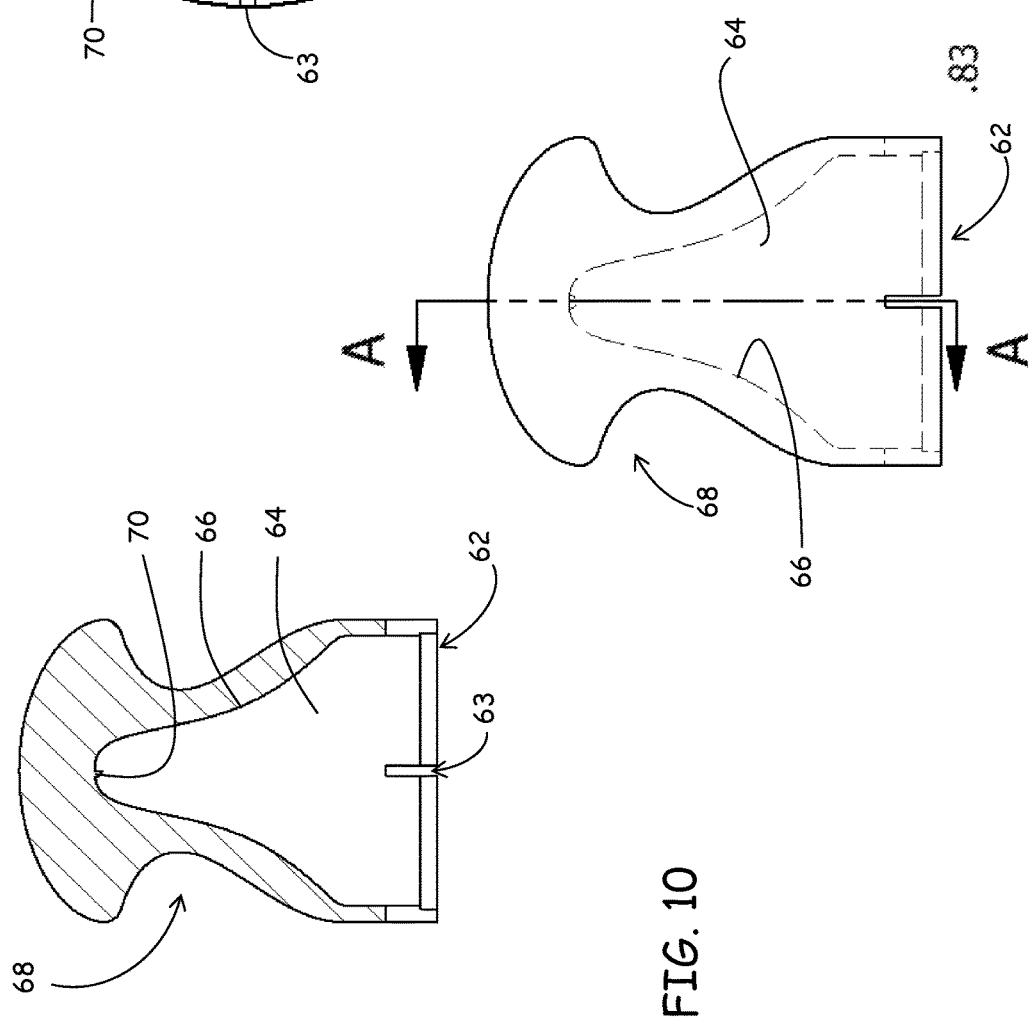
FIG. 10
FIG. 11
FIG. 12

ASSEMBLY AND METHOD FOR DELIVERY OF MICRO-VOLUME DROPLETS FROM A SQUEEZE BOTTLE

CROSS REFERENCE TO RELATED APPLICATION

The present application is based on and claims the benefit of U.S. provisional patent application Ser. No. 62/621,052, filed Jan. 24, 2018, the content of which is hereby incorporated by reference in its entirety.

BACKGROUND

The present invention relates an assembly for attachment to a container and delivery tip for delivery of droplets of fluid therefrom. More specifically, the assembly is securable to a squeeze bottle and configured to reduce the size of droplets of the fluid delivered therefrom.

Ophthalmic solutions including eye drops are available in multidose or single-dose glass and/or plastic dropper bottles that deliver drops with a volume that ranges from 25 µL to 70 µL with an average drop volume of about 40 to 50 µL. The precorneal tear film of the human eye has a lower capacity meaning that for some medications, the optimal drop volume may be much closer to about 10 µL or less. Thus, a significant volume is wasted with each drop. Moreover, when the solution is a prescription medication, the contents may be irritating to surrounding areas of the eye as the excess volume generally ends up in contact with the delicate skin near the eye.

Many squeeze-type bottles generally deliver a droplet having a volume of about 50 µL with much of the volume streaking down the user's face after application. In addition to quicker depletion of the contents of the container, this can also result in running of the user's make up or otherwise requiring clean up after use.

Attempts have been made to, especially in the pharmaceutical industry to repackage medications into bottles that dispense smaller droplet sizes. However, there is no product for consumer use in the form of an adapter or attachment to the current dropper bottles.

SUMMARY

An aspect of the present disclosure relates to an assembly for attaching to a container and configured to reduce the volume of a droplet of fluid ejected from the container wherein the assembly is an after-market assembly securable to the container without alteration of the container and wherein the volume of the droplet is reduced on a microliter scale.

In one embodiment the assembly comprises a base for securing a neck of the container; a tip for securing over a dispensing outlet of the container; and optionally a cap for securing over the tip and connecting to the base.

The base is a ring having an opening configured to receive the tip therethrough and secure a perimeter of a bottom opening of the tip to the neck of the container. The tip has an interior cavity configured to fit over the dispensing outlet of the container and an upper portion of the tip has an outlet for ejecting the droplet of reduced volume. The cap comprises a mechanism for sealing the outlet of the tip to prevent leaks or contamination of the container, as well as clogs of the outlet.

The container may be a squeeze type container and wherein the assembly is configured to reduce the volume of the droplet ejected per squeeze to a volume less than about 15 µL. In one embodiment, the assembly is configured to reduce the volume of the droplet ejected per squeeze to a volume of less than about 10 µL.

In a further embodiment the tip may be conical in shape. The tip can be comprised of a flexible and resilient material, such as medical grade silicone.

The base comprises an inner surface for engaging with an outer surface of the tip and an outer surface for engaging with an inner surface of the cap for forming the assembly configured for securing to the container. The container may be a squeeze-type bottle for dispensing eye drops.

Another aspect of the present disclosure relates to a method of reducing a volume of a droplet of fluid ejected from a container. The method comprises providing an after-market assembly for attaching to the container and having an outlet configured to reduce the volume of the droplet of fluid ejected from the container wherein the volume of the droplet is reduced on a microliter scale; and securing the assembly to the container around the original dispensing mechanism of the container such that the assembly covers the original dispensing mechanism of the container.

In one embodiment, securing the assembly to the container comprises inserting the original dispensing mechanism of the container through an opening in a base portion of the assembly and into a cavity in a tip portion of the assembly.

In one embodiment securing the assembly to the container comprises positioning a tip portion of the assembly over the original dispensing mechanism of the container and operably securing the tip to the container with a base portion by coupling the base portion at or near a neck portion of the container.

Squeezing the container to eject a droplet through an aperture in a tip of the assembly wherein the droplet has a fluid volume of about 15 µL or less than about 15 µL. In some embodiments, first removing a cap portion of the assembly from covering the tip and sealing the aperture allows for dispensing of the reduced volume droplet of fluid.

BRIEF DESCRIPTION OF THE DRAWINGS

FIG. 7 is a perspective view of a tip portion of the assembly.

FIG. 8 is a side view of the tip portion.

FIG. 9 is a cross-sectional view of the base taken along line A-A in FIG. 8.

FIG. 10 is a cross-sectional view of the cap taken along line A-A in FIG. 11(10).

FIG. 11 is a side view of a cap portion of the assembly.

FIG. 12 is a bottom view of the cap.

DETAILED DESCRIPTION

Described herein is an assembly for attachment to a fluid container for modification of the volume of the fluid delivered therefrom. More specifically, the assembly is connectable to a fluid container and configured to reduce the volume of a droplet ejected from the fluid container. The assembly reduces the volume of the droplet ejected from the container without requiring modification of the container, for example, the assembly fits the container as an after-market attachment. No parts of the container need to be modified or removed for the assembly to attach to the container and reduce the volume of the droplets therefrom. The assembly fits over or otherwise connects to the container as manufactured.

The assembly is configured for attachment to a container having elastically deformable walls such as a plastic squeeze bottle or the like. Containers configured for dispensing droplets of fluid including suspensions such as eye drops, and other squeeze style dropper bottles, are within the scope of this disclosure. The assembly is configured to deliver a controlled and reduced droplet size (by volume) of a fluid such as a medicated, prescription, or non-prescription ophthalmic fluid including eye drops, when the assembly is installed on a container and the container is squeezed. The terms "bottle" and "container" are used interchangeably throughout this disclosure.

The assembly described herein may be provided to consumers that use medicine that is dispensed from squeeze dropper bottles or containers such as medicated and non-medicated eye drops. That is, the assembly may be an after-market attachment to said bottles. The assembly may be configured to fit over a pre-existing dispensing mechanism or dispensing tip, such as a nozzle, of the container such that in one embodiment, the dispensing mechanism or nozzle is not removed when the assembly is installed. The assembly can thus work with the pre-existing delivery mechanism to deliver droplets having a volume on a microliter scale. Adapting the pre-existing delivery mechanism without removing the mechanism reduces potential contamination or desterilization of the contents of the container, eliminates the need for tampering with the original container and increases the ease of use of the assembly with various pre-existing containers.

Figure 3:
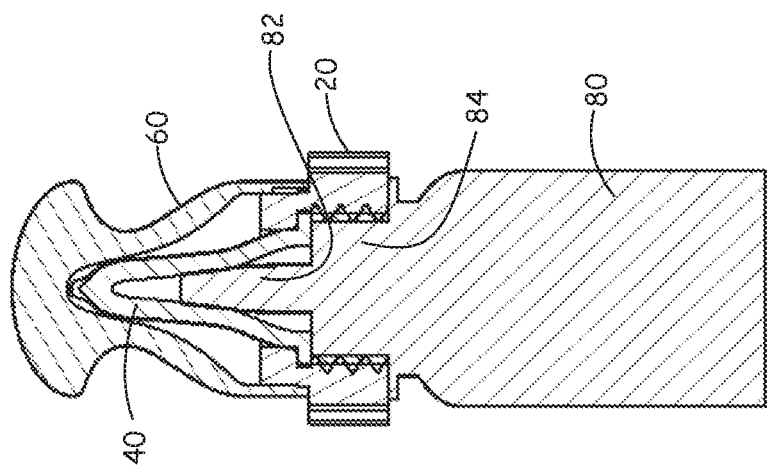
FIG. 3 is a cross-sectional view of the assembly in use taken along line B-B in FIG. 2
Figure 2:
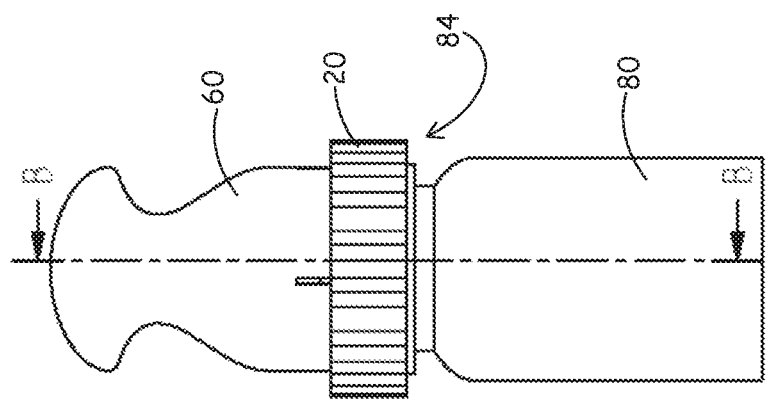
FIG. 2 is a side view of the assembly in use.
Figure 1:
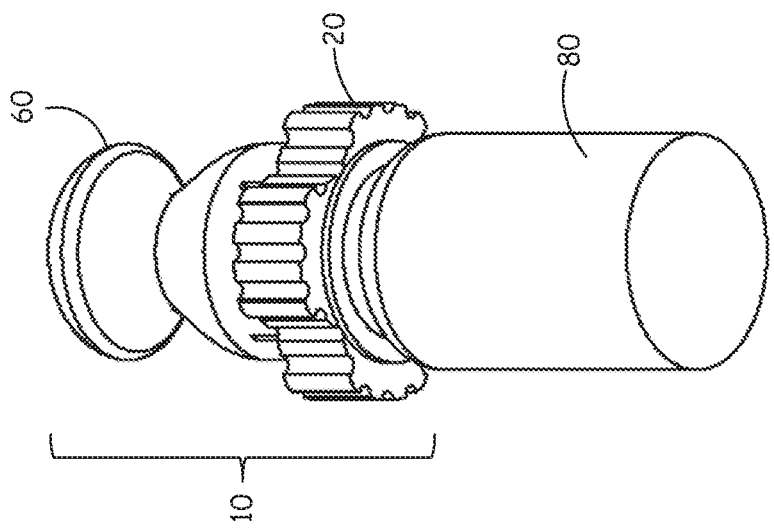
FIG. 1 is a perspective view of an assembly in use with a squeeze bottle for delivery of a liquid or suspension retained in the bottle.

The assembly for securing to a resilient container such as a squeeze bottle or the like is illustrated generally at 10 in FIGS. 1-3. The assembly 10 is configured to deliver a controlled droplet volume, on the microliter-scale, from the container. The assembly 10 delivers substantially consistent volume drops from the container. The assembly 10 is configured for coupling to a container in an after-market manner by the consumer.

Referring generally to the figures, the assembly 10 comprises a base 20, a tip 40, and a cap 60. As illustrated in FIGS. 1-3, the assembly 10 can be secured to a container 80 without removing the nozzle 82 or other dispensing mechanism of the container 80.

Figure 6:
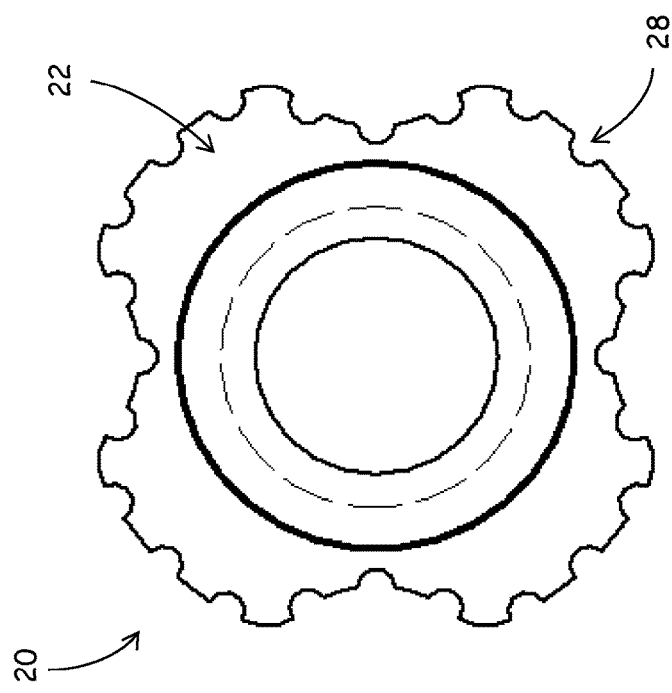
FIG. 6 is a bottom view of the base.
Figure 4:
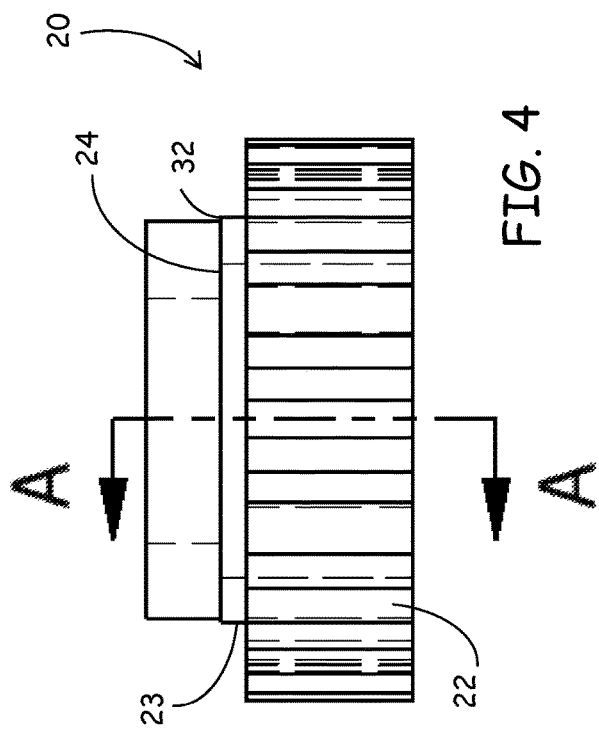
FIG. 4 is a side view of a base portion of the assembly.
Figure 5:
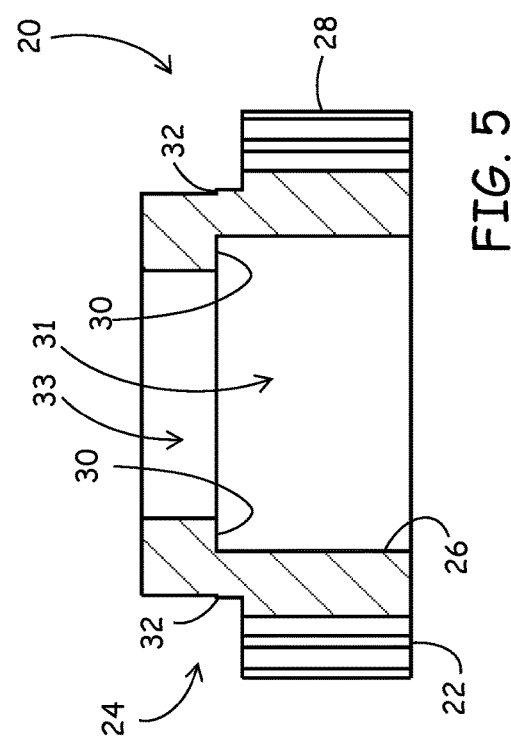
FIG. 5 is a cross-sectional view of the base taken along line A-A in FIG. 4.

As illustrated in FIGS. 4-6, the base 20 has a first end 22 configured to be attached to the container 80 and a second end 24 configured to engage with the tip 40 to secure the tip 40 to the container 80 and the cap 60 to hold the cap 60. In the embodiment illustrated, the base 20 is a ring for engaging with the container 80 at or near the neck 84 of the container or the junction of the reservoir and dispensing tip 82 of the container 80. The lower portion 22 of the base engages with the container 80. For example, an inner face 26 of the lower portion 22 of the ring may have internal threads for securing the base 20 to the container 80. It is also contemplated that the base 20 may have other mechanisms for frictionally engaging or otherwise securing the base 20 to the container at or near the neck 84 or near the base of the dispensing tip 82 of the container 80. The base 20 may have varying inner dimensions so as to allow the base 20 to connect with various standard eye drop delivery bottles 80 and the like. An outer surface 28 of the base 20 may have a perimeter shape allowing for easy gripping of the base during installation and removal of the assembly 10.

The second end 24 of the base 20 has an inner surface 30 that is configured to engage with an inlet portion 44 of the tip 40 for securing the tip 40 to the base 20. The second end 24 also has an outer surface 32 configured to mate with an inner surface of the cap 60 to secure the cap 60 over the tip 40 and to the base 20. For example, the inner surface 30 may be a ledge that fits over a portion of the tip 40 to hold the tip 40 when the assembly 10 is installed on the container 80. The dimensions of the second end 24 at or near the inner surface 30 may provide an opening 31 having dimensions smaller than the dimensions of the lower end 48 of the tip 40 to securely the hold the tip 40 therein. The outer surface 32 may also be a ledge or other surface configured to mate with or couple to a corresponding surface on the cap 60 to hold the cap 60 in place on the base 20.

For example, the outer surface of the base 20 may have one or more outer dimensions of decreasing size such as a first end 22 being larger than a third, middle portion 23 which is larger than the second end 24. Internally, the dimensions of the base 20 include the opening 31 which is larger than opening 33 in the base 20. The tip 40 is secured at its base at least partially inside opening 31 which also receives the neck 84 of the container 80. The tip 40 extends into and through opening 33 as may the delivery mechanism 82 depending on the size and style of the delivery mechanism 82.

The tip is a flexible member having an interior cavity for receiving the dispensing mechanism provided with the container therein. There may be minimal open space in the interior cavity between the inner surface of the tip and the dispensing mechanism of the container. The tip is generally constructed from a flexible and resilient material to allow the tip to fit over the dispensing mechanism of various containers while also reducing the volume of the droplet ejected from the container via an outlet of the tip.

In further detail, as illustrated in FIGS. 7-9, the tip 40 has an internal cavity 42 configured to fit over the dispensing mechanism 82 of the container 80. It is also contemplated that the tip 40 can function in substantially the same manner as described herein with a container having one of various nozzles, tips, or dispensing mechanism styles and is adaptable for use with container of varying outlet sizes. The tip 40 is a strong but flexible tip 40 that fits over the dispensing mechanism 82 and covers the dispensing mechanism 82.

The tip 40 is a unitary hollow construction having an inlet end 44 and an outlet end 46. The inlet end 44 is configured for securing to the container 80 and has dimensions sufficient to allow the inlet end 44 to receive the dispensing mechanism, tip, or nozzle 82 of the container 80 in the cavity 42. The inlet end 44 may have a lip 48 or other perimeter ring extending outwardly from an opening 50 of the inlet end 44 and which engages with the base 20. The inlet end 42 is positionable at or near the base of the dispensing mechanism 82 of the container 80 and is held in place by engagement of the lip 48 with the inner surface 30 of the upper portion 24 of the base 20. For example, the inner surface 30 may be a ledge that rests or provides downward pressure on a top surface of the lip 48 and compresses the lip 48 between the base 20 and surface of the container 80 to removably, but securely hold the tip 40 in place in an upright manner with respect to the container 80.

The outlet end 46 of the tip 40 has a tapered apex 52 having a substantially centered aperture 54 therein for dispensing micro-sized droplets of the fluid from the container 80 therethrough. The aperture 54 has dimensions smaller than the opening in the inlet end 42. In further detail, fluid from the container enters from an inlet side of the aperture 54 and exits from an outlet side of the aperture, where the aperture 54 has a tube or conical surface area between the inlet and outlet of the aperture 54. The length of the surface area corresponds to a wall thickness of the tip 40 such that the aperture 54 provides a fluid flow regulating mechanism where the surface area of the wall prevents the fluid from freely streaming out of the aperture 54. In one embodiment the cross-sectional dimensions of the inlet side of the aperture 54 are different than the cross-sectional dimensions of the outlet side of the aperture 54 for controlling flow of the fluid from the container 80 through the tip 40 and out of the aperture 54. For example, the outlet side of the aperture 54 may be smaller or larger than the inlet side of the aperture 54. The surface area of aperture 54 defines the drop volume by controlling the surface tension of the fluid ejected.

The tip 40 may be tapered along a height or otherwise conical in shape as illustrated. The tip 40 is comprised of a durable but flexible material, examples of which include but are not limited to medical grade silicone. The tip 40 can be stretched at the inlet end 42 to fit on stock or standard size squeeze bottles 80 and to form a seal around the neck portion 84 of the bottle 80 and to minimize dead space around the dispensing mechanism 82 of the bottle 80. The tapered or conical shape of the tip 40 from the inlet end 42 to the outlet end 44 allows for the reduction of the volume dispensed per droplet when the squeeze bottle is squeezed for fluid delivery. That is, the size of the droplet delivered per squeeze is reduced. For example, the outlet aperture 54 of the tip 40 may have an inner diameter about the size of a 20 to 22 gauge needle for dispensing a droplet therethrough with each squeeze of a bottle 80 with which the tip 40 is secured to.

The tip 40 may be configured with outlet aperture 54 dimensions sufficient to dispense a droplet volume in the range of about 5 µL to about 30 µL, and more specifically in the range of about 7 µL to about 20 µL, and more specifically in the range of about 9 µL to about 15 µL per droplet. The dimensions of the aperture 50 may produce a droplet per squeeze having a volume of less than about 30 µL and more specifically less than about 20 µL and more specifically less than about 15 µL per droplet. Moreover, the tip 40 when secured by the base 30 to the container 80, is configured to deliver consistent size (volume) drops.

As illustrated in further detail in FIGS. 10-12, the cap 60 is configured to removably secure over the tip 40 and connect to the base 20. The cap 60 is a hollow construction that may be tubular or conical in shape and has an open lower portion 62 for fitting over the tip 40 and engaging with the base 20. The cap 60 has a tapered inner cavity 64 such that a portion of the cap 60 intended to cover the tip 40 has dimensions configured to at least partially mate with and contact the upper portion 46 of the tip 40. An inner surface 66 of the upper portion 68 of the cap 60 is configured with a tip sealing mechanism 70 which may be a tab, plug, protrusion, film, flange or other mechanism for engaging with or otherwise covering, sealing or plugging the aperture 54 of the tip 40 to provide a water tight seal the tip 40.

In the embodiment illustrated, the sealing mechanism 70 is a tab having outer dimensions that mate with the inner dimensions of the aperture 54 so that the sealing mechanism catches and plugs the aperture 54 when the cap 60 is secured to the base 20. The cap 60 may be comprised of a plastic material such as high-density polyester (HDPE) or other plastic or like materials. The sealing mechanism 70 may also prevent clogging of the aperture 54 as some fluids ejected from containers to which the assembly may be installed include suspensions and colloids where particles including salts may clog the outlet after repeated use. The sealing mechanism may also clear the aperture 54 preventing clogs.

The upper portion 68 of the cap 60 may be configured with an ergonomic outer surface to provide for easy gripping and installation or removal of the cap 60.

The lower portion 62 of the cap 60 is a perimeter ring for the cavity 64 that may have one or more tabs or slits 63 provided therein and spaced apart along the perimeter of the portion 62. As illustrated, the slits 63 allow for the coupling of the cap 60 at the lower portion 62 to the outer surface 32 of the base 20. The cap 60 is thus removable from the base 20.

As illustrated in the embodiments described herein, the assembly comprises three separable components in the base 20, tip 40, and cap 60. The base 20, tip 40, and cap 60 are all removably securable to a container as an after-market assembly. That is, the assembly 10 can be used, and in some embodiments re-used, with various size and style squeezable containers without removal of the original dispensing mechanism or nozzle of the container 80.

The assembly 10 described herein is configured for attachment to a container 80. While one method of operably securely attaching or coupling the assembly to the container 80 is described hereinafter, alternative methods of operably securely attaching or coupling the assembly to the container are contemplated and within this disclosure. Securing the assembly may comprise snapping or rotating the base to attach the base to the container or otherwise frictionally engaging the assembly 10 with the container 80.

In one embodiment, a method of securing the assembly 10 to a container 80 comprises connecting the tip 40 to the base 20 by inserting the tip 40 into the base 20. The lip 48 frictionally engages with and is held by the base 20. The cap 60 is then secured over the tip 40 and engaged or connected with the base 20. The base 20 is placed over the delivery mechanism 82 of the container 80 so that the tip 40 is also placed over the delivery mechanism 82. The base 20 is secured around the neck 84 of the container 80. For example, the base 20 may be rotated to tighten the base 20 around the neck 84. The cap 60 can then be removed and the container 80 squeezed to deliver a microliter volume per droplet of contents from the container 80. The assembly 10 can be secured to a pre-existing squeeze bottle without exposing the tip 40 prior to use and without removal or other handling of the delivery tip 82 of the container 80. As the base 20 is secured on or around the neck 84 of the container 80, the lip 48 of the tip 40 is stretched and/or compressed around the neck 84 of the container 80 between the container 80 and the base 20 to provide a seal and air tight connection between the assembly 10 and the container 80.

The assembly as provided may include the cap 60 already secured over the tip 40 wherein the lower portion 62 of the cap 60 is engaged with the base 20 and thus provides a capped and sealed assembly to the container 80. This prevents fluid leaks from the container 80 and prevents contamination of the contents of the container 80, as well as the tip 40, thus retaining the sterile nature of the contents.

The cap 60 is removable and the container 80 squeezable to deliver a droplet having a volume in the ranges described above and more specifically in the range of about 9 μL to about 15 μL through the tip. The cap 60 is replaceable between uses.

In one embodiment, the base 20, tip 40, and cap 60 may also include washable components such that the assembly 10 can be removed, cleaned and re-used with subsequent bottles 80 of fluid.

In one embodiment, the base 20, tip 40, and cap 60 may be disposable components such that the assembly 10 can be removed and disposed of after use with a bottle 80 of fluid.

The assembly described herein allows for the reduction of overdosing which can cause adverse side effects that range from minor annoyances such as foul taste and smudging makeup to serious systemic effects on heart health such as causing bradycardia and arrhythmias. The reduction in droplet volume on the microliter scale described herein also reduces the user's exposure to the preservatives contained in many ophthalmic fluids for treatment of various conditions delivered via the squeeze bottles described herein.

The embodiment illustrated is an assembly 10 that is a one-size fits most assembly 10 for securing to a plastic dropper bottle 80. However, the assembly may be similarly installed on various resilient containers for fluid dispensing where the container is a squeeze type or similar container and is not limited to use in connection with eye-drops or ophthalmic medicaments.

Although the present disclosure has been described with reference to preferred embodiments, workers skilled in the art will recognize that changes may be made in form and detail without departing from the spirit and scope of the disclosure.

The invention claimed is:

1. An assembly having a flexible and resilient tip for attaching to a container and configured to reduce a volume of a droplet of fluid ejected from the container wherein the assembly is removably securable to the container without removal of a dispensing tip original to the container, wherein the container is a squeeze type container and wherein the volume of the droplet ejected from the container is reduced on a microliter scale as the assembly is configured to reduce the volume of the droplet ejected per squeeze to a volume less than about 15 μL.

2. The assembly of claim 1 wherein the assembly comprises:
a base for securing to neck of the container;
the tip for securing over the dispensing mechanism of the container; and
a cap for securing over the tip and connecting to the base.

3. The assembly of claim 2 wherein the base is a ring configured to receive the tip therethrough and secure a perimeter of a bottom opening of the tip to the neck of the container.

4. The assembly of claim 3 wherein the tip has an interior cavity configured to fit over the dispensing outlet of the container and an upper portion of the tip has an outlet for ejecting the droplet of reduced volume.

5. The assembly of claim 4 wherein the cap comprises a mechanism for sealing the outlet of the tip to prevent leaks or contamination of the container.

6. The assembly of claim 2 wherein the tip is conical in shape.

7. The assembly of claim 2 wherein the tip is comprised of a flexible and resilient material.

8. The assembly of claim 2 wherein the tip is comprised of medical grade silicone.

9. The assembly of claim 2 wherein the base comprises an inner surface for engaging with an outer surface of the tip and an outer surface for engaging with an inner surface of the cap for forming the assembly configured for securing to the container.

10. The assembly of claim 2 wherein the tip comprises a dispensing aperture having dimensions configured to control a flow of drops per squeeze of the container and control a volume of a drop ejected therefrom.

11. The assembly of claim 1 wherein the assembly is an after-market assembly for securing to the container without alteration of the container.

12. The assembly of claim 1 where a lip portion of the tip is stretched or compressed between the container and a base of the assembly to provide a seal and air-tight connection between the assembly and the container.

13. A method of reducing a volume of a droplet of fluid ejected from a container, the method comprising:
providing a multi-component assembly for removably attaching to the container over an original dispensing mechanism of the container and the assembly having an outlet configured to reduce the volume of the droplet of fluid ejected from the container
wherein the volume of the droplet is reduced on a microliter scale; and
securing the assembly to the container around the original dispensing mechanism of the container such that the assembly covers the original dispensing mechanism of the container,
wherein the multi-component assembly comprises an interconnectable base and tip and wherein the tip comprises a lip such that the base removably engages with the lip to secure the tip to the container; and
squeezing the container to eject a droplet through an aperture in the tip of the assembly
wherein the droplet has a fluid volume of less than about 15 μL.

14. The method of claim 13 wherein securing the assembly to the container comprises inserting the original dispensing mechanism of the container through an opening in the base portion of the assembly and into a cavity in the tip portion of the assembly.

15. The method of claim 13 wherein securing the assembly to the container comprising positioning the tip portion of the assembly over the original dispensing mechanism of the container and operably securing the tip to the container with the base portion by coupling the base portion at or near a neck portion of the container.

16. The method of claim 13 and further comprising a removable cap independent of the base and tip and for selectively securing over the tip and removing the cap portion of the assembly from covering the tip and sealing the aperture.

17. The method of claim 13 wherein the tip is comprised of silicone.

18. An assembly for attaching to a container and configured to reduce the volume of a droplet of fluid ejected from the container, the assembly comprising:
a base element for securing to a neck of the container;
a flexible dispensing tip for securing over a nozzle original to the container and configured to reduce a volume of a droplet ejected from the container on a microliter scale such that the droplet has a fluid volume of less than about 15 μL; and
a cap for securing over the tip and connectable to the base, wherein the base element has an opening configured to receive the tip and nozzle therethrough and a surface to secure a perimeter lip of a bottom opening of the tip to the neck of the container such that the tip is removably secured over the nozzle by the base element.

19. The assembly of claim 18 wherein the base element, tip, and cap are separable components provided as an assembly and wherein at least one of the base element and cap are constructed of a material different than the tip.

\* \* \* \* \*